United States Patent [19]
Gabbay

[11] Patent Number: 5,599,329
[45] Date of Patent: Feb. 4, 1997

[54] MULTI PURPOSE PERFUSION CANNULA

[76] Inventor: Shlomo Gabbay, 1 Randall Dr., Short Hills, N.J. 07078

[21] Appl. No.: 200,211

[22] Filed: Feb. 23, 1994

Related U.S. Application Data

[62] Division of Ser. No. 992,116, Dec. 17, 1992, Pat. No. 5,330,451.

[51] Int. Cl.⁶ .................................................. A61M 25/00
[52] U.S. Cl. ............................ 604/284; 604/49; 606/158
[58] Field of Search ............................... 604/284, 51–53, 604/49; 606/157, 158

[56] References Cited

U.S. PATENT DOCUMENTS

| | | | |
|---|---|---|---|
| 4,592,339 | 6/1986 | Kuzmak et al. | 604/157 X |
| 4,592,355 | 6/1986 | Antebi | 604/157 X |
| 4,881,939 | 11/1989 | Newman | 604/158 X |

*Primary Examiner*—John D. Yasko
*Attorney, Agent, or Firm*— Bierman and Muserlian

[57] ABSTRACT

A perfusion cannula for insertion into an artery having a main channel fluidly connected to an intra-aortic portion and in fluid connection with an aortic perfusion line of a cardiopulmonary bypass. The cannula includes a first side port to which an extra-aortic balloon pump may be connected or through which an intra-aortic balloon pump may be inserted. Also, there is a blood pressure port which can be connected to a blood pressure monitoring device without removal of the cannula.

21 Claims, 8 Drawing Sheets

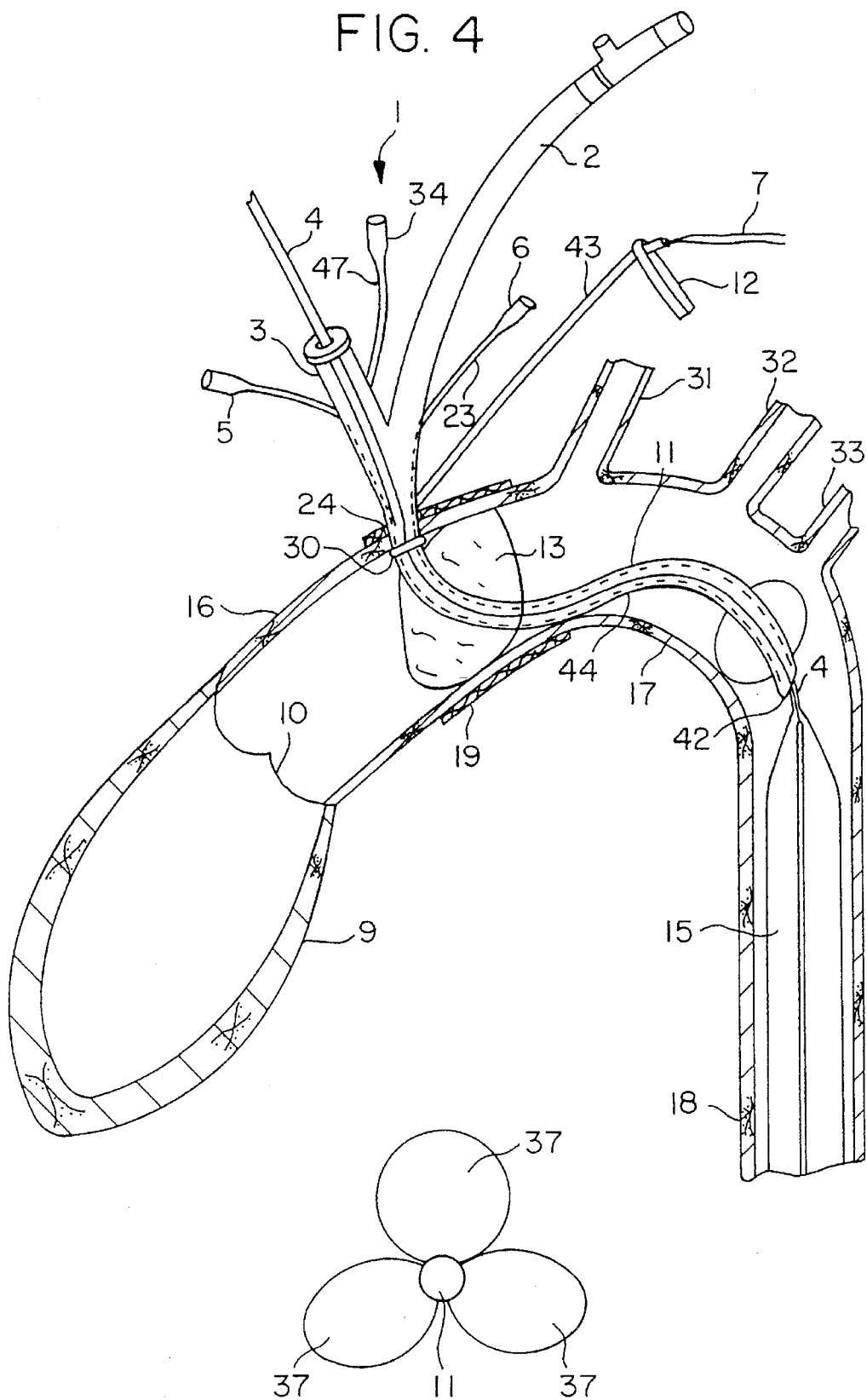

MULTI PURPOSE PERFUSION CANNULA

PRIOR APPLICATION

This application is a division of U.S. patent application Ser. No. 992,116 filed Dec. 17, 1992, now U.S. Pat. No. 5,330,451.

The present invention is directed to an improved perfusion cannula, more particularly one for use in the aorta during open heart surgery.

BACKGROUND OF THE INVENTION

The nature of the population for open heart surgery is rapidly changing; in recent years, an increasing number of high risk patients are being brought to the operating table for this procedure. There are a number of reasons for this.

In general, such patients are substantially older than before. Specifically, the mean age is approximately seventy-one years while, only twelve years ago, the mean age was only fifty-one years. In essence, the problems arise as a result of the success of other treatments. Improvements in medical treatment have resulted in the availability of a wide range of cardiac drugs which will prevent angina, thereby permitting patients to survive longer, even though heart problems are present. In addition, angioplasty and arterectomy of single, double, and even multiple vessels are commonplace; thus, many patients come to surgery only after several other cardiac procedures have been carried out. In addition, the percentage of second operations performed on the same patient is also increasing. In some areas, it is as high as 10% to 30%; this is because patients are surviving longer after the first operation.

Thus, patients seeking open heart surgery are much sicker and frailer than they ever were. They present higher risks and, of course, increased anxiety on the part of both the patient and the surgeon. Hence, the use of such expedients as the intra-aortic balloon has been rising steadily. This device is used to assist, on a temporary basis, the failing heart after surgery is completed.

In almost every case of coronary artery bypass surgery, the internal mammary artery (IMA) is used. This artery tends to become narrower when the blood pressure falls just after all the grafts have been anastomosed and the aortic cross pump removed. This phenomenon is called arterial spasm. This is extremely detrimental to the patient since it does not permit good perfusion of the left heart, thus reducing blood pressure even further. The fact that the IMA is usually implanted in the left anterior descending artery of the heart is a contributing factor. A vicious cycle is created and must be treated immediately by insertion of an Intra-Aortic Balloon Pump (IABP), drugs, or even the insertion of an additional graft, taken from the saphenous vein, into the left anterior descending artery. If treatment is not carried out promptly, the patient may die.

A further problem resides in the age of the patients and the condition of their arteries. It is common to find diffuse atherosclerosis in such patients, as well as aortas which are seeded with calcified plaque. Thus, the risk of stroke is substantially increased because, if a small piece of calcium is dislodged, it can easily be carried to the brain as an embolism through, for example, the brachiocephalic artery. This can occur as a direct result of certain mechanisms; specifically, cross clamping of the ascending aorta to isolate and cool the heart for the surgery. Another cause is the jet of blood exiting from the aortic cannula which can, if it impinges on the walls of the aorta, dislodge plaque therefrom, especially in the region of the aortic arch. Moreover, this area generally has greater calcium deposits than any other part of the aorta.

Many of the patients suffer from peripheral atherosclerosis, wherein the femoral arteries are extremely narrowed or even fully occluded. This condition makes the introduction of the IABP through that artery virtually impossible or, at best, at high risk with a strong likelihood of complications. There also are occasions when heart failure occurs under conditions such that the IABP and drugs are insufficient to maintain the patient. In such situations, an extra-aortic pump (EAP), particularly one which will be activated and controlled by the existing IABP console, can be effective. While the IABP can increase coronary blood flow by 5% to 15% the EAP can increase the flow by 100% or more.

Still another problem relates to the perioperative monitoring of the patient's blood pressure. This can be extremely difficult, and sometimes even impossible, the use of either the radial or femoral artery.

SUMMARY OF THE INVENTION

It is among the objects of the present invention to provide a means whereby an intra-aortic balloon, in conjunction with the IABP console, can be used to assist the failing heart, especially during open heart surgery, thereby preventing many possible complications. The IABP can be used for such high risk patients as those suffering from (1) severe left main coronary artery disease, (2) failed angioplasty, (3) failed arterectomy, (4) low ejection fraction, (5) intractable angina, (6) severe triple vessel coronary disease, (7) repeat coronary artery bypass grafting, (8) prevention of IMA spasm, (9) post-operative crisis, (10) temporary post-operative low output syndrome, and (11) in any situation in which introduction of the balloon through the femoral arteries is inadvisable or impossible.

There are also situations wherein the intra-aortic balloon pump is insufficient to sustain the patient. Therefore, the present invention provides a means whereby an extra-aortic pump can be quickly connected directly to the cannula for immediate operation. Moreover, the extra-aortic pump can also be used to convert a cardiopulmonary bypass to a pulsatile bypass, thus minimizing the onset of complications which result from non-pulsatile bypasses. The pump can be used in severe post-operative heart failure and, if the patient is temporarily dependent on the pump, the device can be inserted directly through the ascending aorta after the cannula has been removed.

The present invention also permits monitoring blood pressure deep inside the aorta. This can be done while the IABP or extra-aortic pump is operational, as well as while the patient is on the cardiopulmonary bypass.

It is further among the objects of the present invention to provide a cannula which is designed to prevent or minimize. dislodgment of calcium particles in aortas which are severely calcified. The cannula of the present invention is provided with an inflatable balloon which acts to occlude the aorta adjacent the heart. This isolates the latter and obviates the need for cross clamping. Cross clamping and dislodgment of debris by the cannula are the two main reasons for the formation of calcium embolisms, a major cause of stroke. The device eliminates the need to cool the patient to extreme low temperatures, nor is it necessary to perform the operation with complete circulatory arrest. The latter, in particular, carries a very high morbidity.

The present invention provides a cannula which, while it will be described in connection with aortic perfusion, is capable of uses elsewhere as well. In its simplest form, it comprises a perfusion cannula especially adapted for insertion into the aorta. There is a main channel which is fluidly connected at one end to an intra-aortic portion of the cannula and, at the other end, is fluidly connected to the aortic perfusion line of a cardiopulmonary bypass. There is also provided a first side port which can be fluidly connected to an extra-aortic pump or to an intra-aortic balloon pump. The other end of the first port is in fluid connection with the intra-aortic portion of the cannula. This arrangement permits the insertion of the intra-aortic balloon pump through the first port, into the intra-aortic portion of the cannula, and beyond into the descending aorta.

A blood pressure port is also provided which is fluidly connected to a blood pressure monitoring tube. The tube, in turn, is located within the intra-aortic portion and extends therein to a pressure point which is upstream of the distal end of the portion. The other end of the tube is adapted for connection to a blood pressure measuring or monitoring device.

The cannula is inserted in the aortic arch and, in the primary embodiment of the invention, extends a relatively short distance longitudinally of the aorta. Advantageously, in this form of the cannula, the portion may terminate approximately opposite the brachiocephalic artery. The end of the first port remote from the portion may have a plug located therein. Within the plug is a one-way valve which prevents outward flow of blood, but permits insertion of the intra-aortic balloon. The balloon is controlled by a console which electronically monitors the heart beat and expands and contracts the balloon in synchronism therewith. Since the extra-aortic pump displaces a much greater volume than does the IABP, because it is close to the coronary arteries, it is necessary to remove the plug (along with the valve) before attaching the extra-aortic pump to the cannula.

In another embodiment of the invention, an inflatable occlusive balloon surrounds at least part of the intra-aortic portion of the cannula. In this modification, the first port is also fluidly connected to the occlusive balloon and adapted for connection to an intra-aortic balloon pump, as well as to a control device therefor. The IABP console can operate the extra-aortic pump, as well.

In a third form of the device, the occlusive balloon is provided as previously described. In addition thereto, an inflatable non-occlusive balloon surrounds the intra-aortic portion at or adjacent the distal end thereof. The portion is longer than in the first two embodiments and the distal end is located in the descending aorta. The non-occlusive balloon serves two purposes. First, it acts as a guide to lead the intra-aortic portion around the curve of the aortic arch into the descending aorta. It minimizes the contact between the distal end of the portion and the anterior wall of the aorta. In this way, the likelihood of dislodgment of a calcium particle is reduced.

Second, since the main channel and the intra-aortic portion constitute or contain a blood passage, the presence of the non-occlusive balloon centers the exit of the blood passage so that the stream of perfused blood coming from the cardiopulmonary bypass is substantially parallel to the walls of the descending aorta. As a result, impingement of the stream on the walls is kept to a minimum. This, too, substantially reduces the risk of calcium particles being dislodged.

It has been found advantageous, when using the various embodiments of the present invention, to provide a girdle around the aorta. This is a strip of material which is wrapped around the aorta in order to reinforce it and prevent rupture of the artery wall. It is provided with strings attached to the ends whereby it can be tied in place. It is also provided with a hole through which the cannula of the present invention can be inserted. The girdle is tied to the aorta, and the surgeon stitches the girdle to the aorta immediately around the hole, prior to insertion of the cannula. It has been found advantageous to use a "purse string suture" which, after the cannula has been inserted, will pull the edges of the aortic opening closely around the cannula, thereby minimizing blood loss.

Preferably, the girdle should be made of either an inelastic material or one which is only slightly elastic. Since the material is to act as a reinforcement of the aorta, it should not be too elastic, as this would interfere with its primary function. After the surgery is complete, the girdle may be left in the patient as a permanent reinforcement. The material may be Dacron, Teflon, or any other suitable biological or prosthetic material. Xenograft pericardium has been found quite useful.

A further advantage of the girdle is that it can comprise a fabric graft (preferably about 6 mm in length) sewed thereto to carry a blood pressure sensor below the sternum to the skin surface. The intra-aortic balloon can be removed and the wound closed. The projecting graft portion then provides a means whereby the blood pressure of the patient can be continuously monitored. When this is no longer required, the outer end is buried in the skin and sewn in place.

When a cannula is inserted into an artery, particularly the aorta, there is always the danger of the introduction of an air bubble. Should this be carried to the brain, a stroke could result. It is, therefore, of primary importance that this be prevented.

To assist in doing so, there is provided a trocar which is flexible and moves axially within the cannula itself. The trocar is hollow and contains a guide wire by which the surgeon is able to manipulate it and minimize or avoid damage to the artery walls.

The trocar terminates, at its inner end, in a head which comes to a point. After the surgeon has made the initial incision in the artery, the point of the trocar is inserted to dilate the opening. To facilitate the elimination of air, the head contains holes, preferably one at each of the upper and lower surfaces of the head and one at the point, to allow air and blood to pass through the head to the rear portion of the trocar. The air, along with some blood, is permitted to leak out of the cannula due to the imperfect fit between the guide wire and the plug at the outer end. When the trocar is almost completely withdrawn, the cannula is clamped to prevent any further loss. Thereafter, the trocar is completely removed and the cannula is connected to the perfusion line of a cardiopulmonary bypass. This eliminates or minimizes the risk of an air bubble getting to the brain of the patient. Moreover, it also minimizes blood loss.

BRIEF DESCRIPTION OF THE DRAWINGS

In the accompanying drawings, constituting a part hereof, and in which like reference characters indicate like parts.

FIG. 4 is a view similar to that of FIG. 1 of the embodiment of FIG. 3 with an intra-aortic balloon in the descending aorta;

FIG. 5 is a schematic sectional view of the non-occlusive balloon;

DETAILED DESCRIPTION OF THE INVENTION

Figure 1:
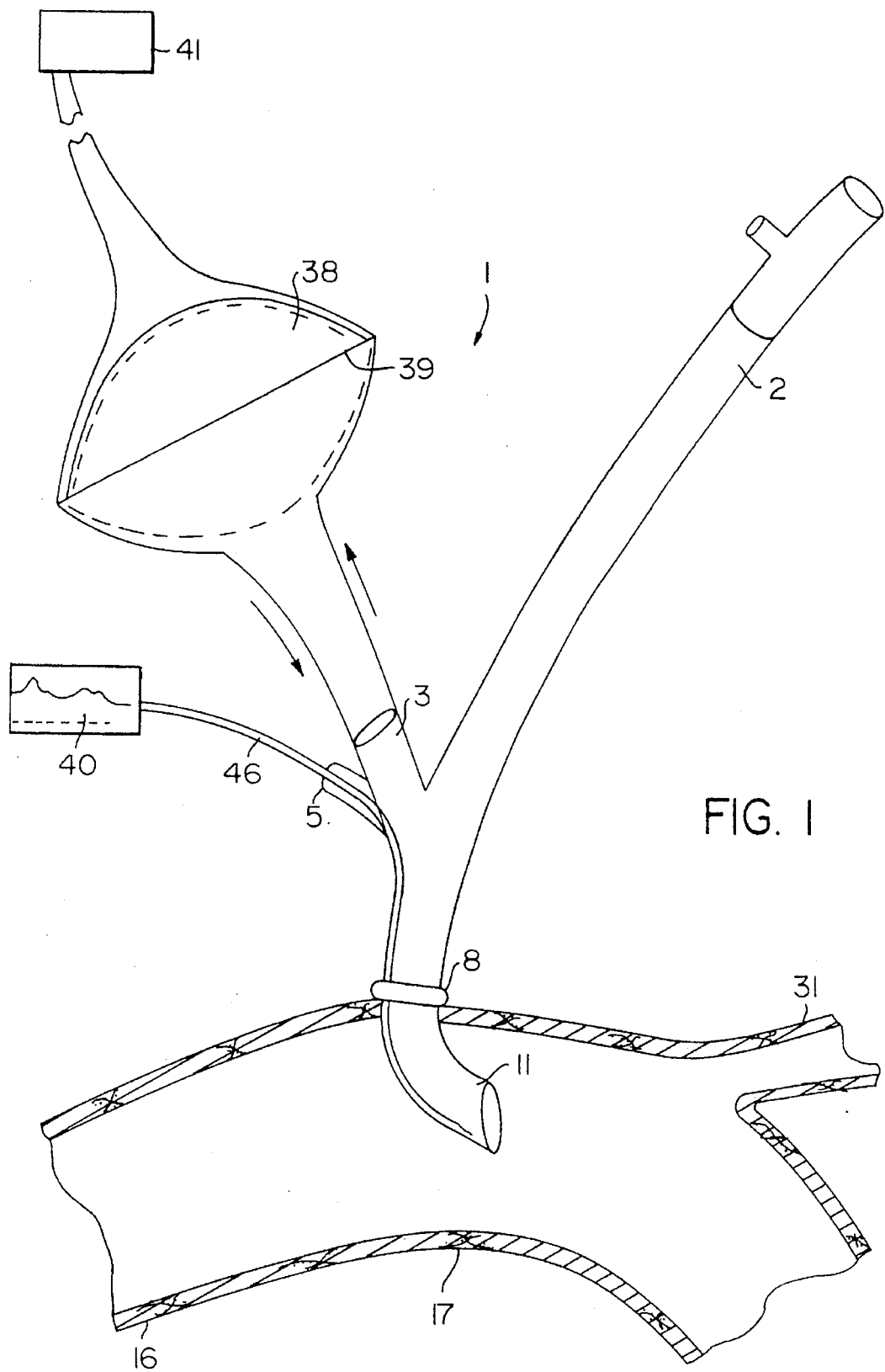
FIG. 1 is a schematic view, partly in section, of the first embodiment of the present device with the intra-aortic portion located in the aorta.

Referring particularly to FIG. 1, cannula 1 comprises main channel 2, intra-aortic portion 11, first side port 3, and blood pressure port 5. Main channel 2 is connected to the aortic perfusion line of a cardiopulmonary bypass (not shown) and carries the perfused blood into intra-aortic portion 11. First port 3 is connected to extra-aortic pump 38 which includes diaphragm 39. The pump alternately pumps blood in and withdraws it and is controlled by console 41.

Blood pressure port 5 receives blood pressure tube 46 which extends within cannula 1 to opening 44 adjacent the distal end of intra-aortic portion 11. When opening 44 is located in this manner, the blood pressure reading is not influenced by the flow of blood exiting intra-aortic portion 11. The other end of tube 46 is connected to blood pressure monitor 40.

For the assistance of the surgeon, locator ring 8 is placed on cannula 1 so that the proper depth of insertion can easily be accomplished. The aorta comprises ascending aorta 16, aortic arch 17, and descending aorta 18 (not shown in FIG. 1). Preferably, cannula 1 is inserted into ascending aorta 16 or aortic arch 17, but upstream of brachiocephalic artery 31.

Figure 2:
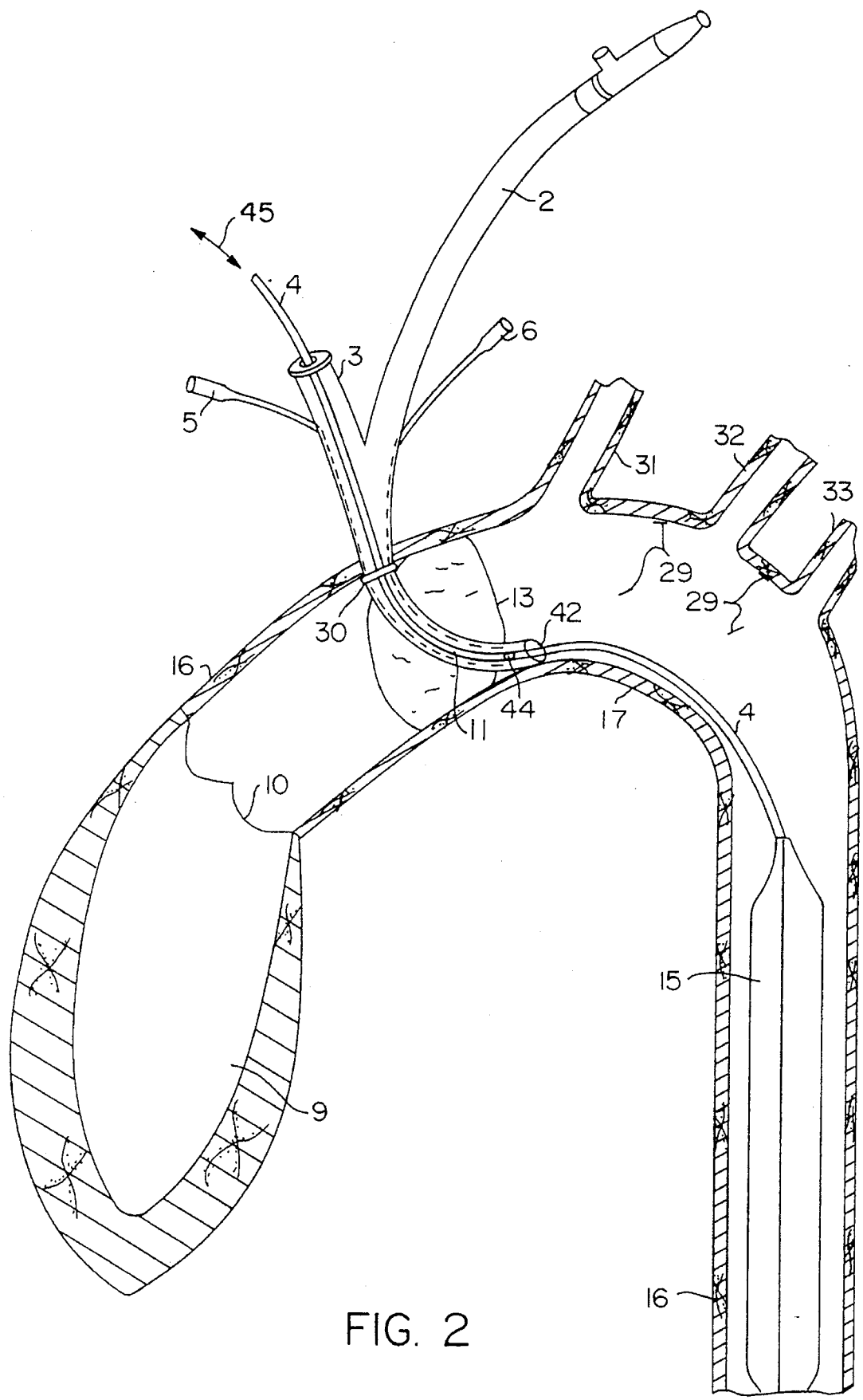
FIG. 2 is a view similar to that of FIG. 1 showing the second embodiment of the invention with the occlusive balloon and an intra-aortic balloon positioned in the aorta.

Another embodiment of the invention is shown in FIG. 2. Cannula 1 comprises main channel 2, intra-aortic portion 11, first side port 3, and blood pressure port 5, all substantially as described with respect to FIG. 1. However, there is provided occlusive balloon 13 which completely blocks ascending aorta 16. This enables heart 9 and aortic valve 10 to be isolated while the surgery is performed. Second side port 6 is provided to introduce and withdraw fluid into and out of occlusive balloon 13. If the blend is air, it increases the risk to the patient, as an air bubble could be formed should balloon 13 rupture. Therefore, it is preferable that a liquid such as saline be used for this purpose. Fluid tube 4 carries the fluid which is used to inflate and deflate balloon 15. This form of the device can be used with intra-aortic balloon 15. This is part of a intra-aortic balloon pump wherein fluid is introduced into and withdrawn from balloon 15 as indicated by arrow 45. The action of the pump is controlled by console 41 (see FIG. 1). Balloon 15 is inserted past brachiocephalic artery 31, carotid artery 32, and subclavian artery 33 into descending aorta 18.

Figure 3:
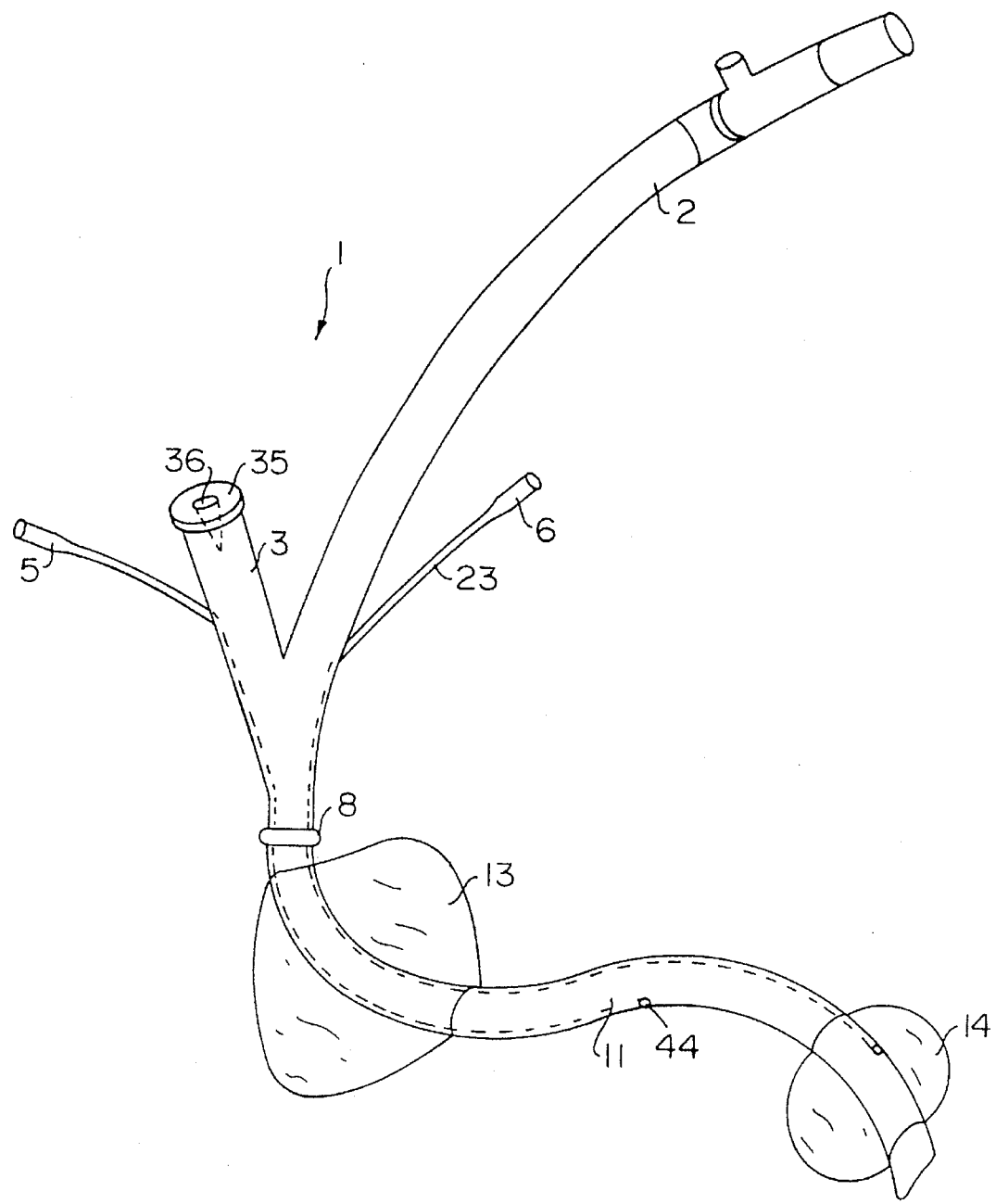
FIG. 3 is a view similar to that of FIG. 1 of the third embodiment of the invention, without the aorta, but with both the occlusive balloon and the non-occlusive balloon in place.

In FIG. 3, still another form of the device is shown, but without particular reference to the aorta in which it may be placed. Cannula 1 is similar to the embodiment shown in FIG. 2, but the intra-aortic balloon is not present. Most of the elements correspond with the device of FIG. 2 and need not be further described here. It should be noted that intra-aortic portion 11 is substantially longer than its corresponding part in the embodiment shown in FIG. 2. Moreover, non-occlusive balloon 14 is provided adjacent its distal end. Second side port 6 is connected to fluid tube 23 which feeds fluid to—and withdraws it from—balloon 14. First side port 3 is provided with plug 35 containing one-way valve 36. Valve 36 prevents blood from flowing out of port 3, but permits the insertion of an intra-aortic balloon pump therethrough, if needed. Port 3 can also receive an extra-aortic pump, but it is necessary to remove plug 35 before the insertion thereof. This is important because the volume of blood pumped by the extra-aortic pump is much larger than that pumped by the intra-aortic balloon pump.

In FIG. 4, the foregoing embodiment is shown in the aorta along with intra-aortic balloon 15. Third side port 34 is connected to fluid tube 47 which carries fluid to and from balloon 14. A cross-section of balloon 14 is shown in FIG. 5. Balloon 14 is provided with lobes 37 and surrounds portion 11. Balloon 14 performs two functions. On insertion of cannula 1 into the aorta, it gently guides portion 11 around the aortic arch past arteries 31, 32, and 33. As a result, the pressure and stress on the anterior wall of the aorta are minimized and the risk of dislodgment of calcium plaque, which is frequently found at that point, is reduced.

In addition to the foregoing, balloon 14 centers the distal end of portion 11 and blood passage 42. Thus, when the perfused blood exits blood passage 42, the stream thereof is substantially parallel to the walls of the descending aorta, it does not impinge to any degree upon those walls and, therefore, the chance of plaque being dislodged is substantially and materially reduced.

Girdle 19 is provided to strengthen and reinforce the aorta. Hole 24 is provided in girdle 19 and sealing ring 30 is located on portion 11. Girdle 19 is sutured to the aorta around the periphery of hole 24. Sleeve 43 slidably surrounds suture 7 so that the surgeon can pull on suture 7 while holding sleeve 43 with forceps 12 to draw the purse string sutures (not shown) and cause the aorta to grip cannula 1 tightly. Thus, between the sutures and ring 30, a good seal is provided so that blood does not leak out.

Figure 6:
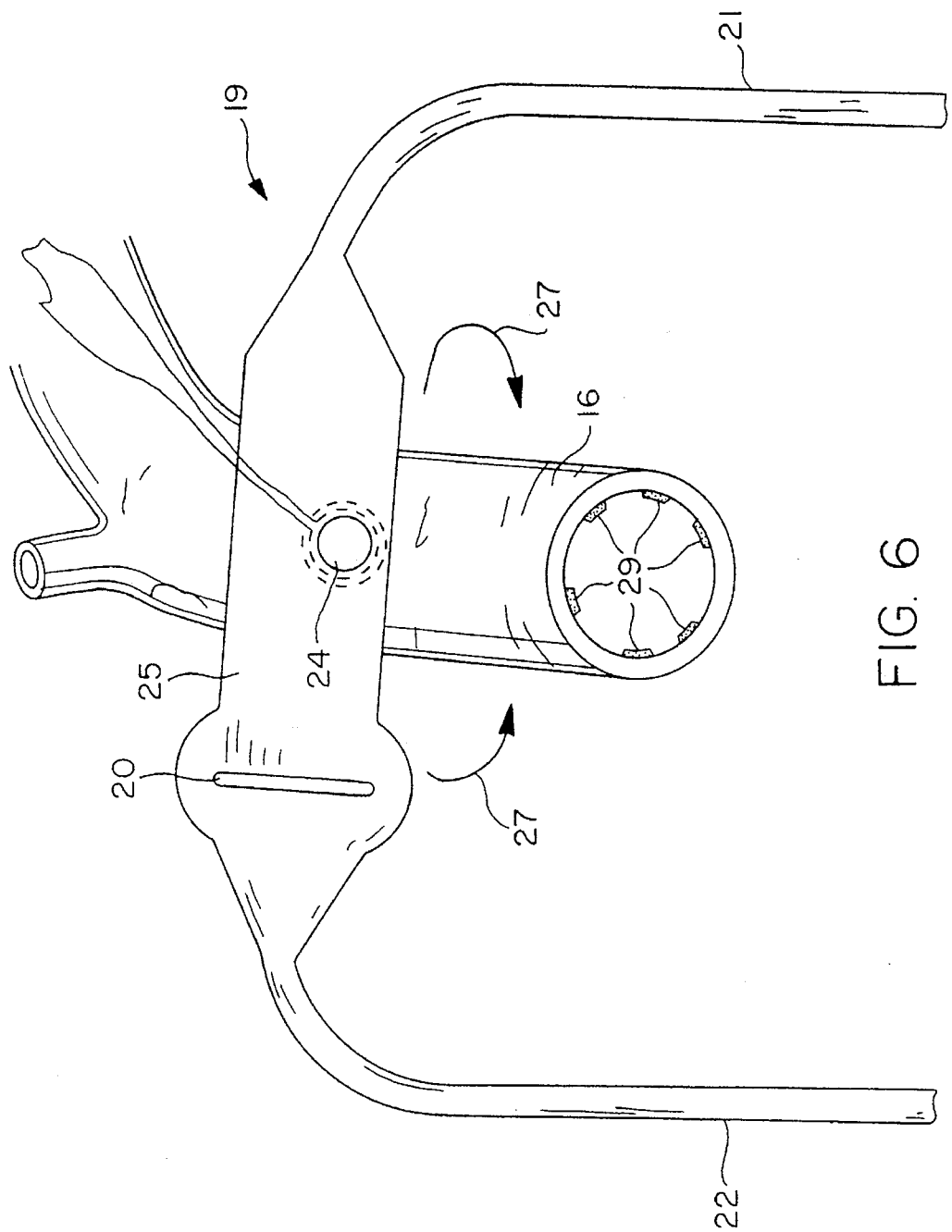
FIG. 6 is a schematic view of the girdle of the present invention after it has been stitched to the aorta but before it has been wrapped therearound.

Girdle 19 is shown in FIG. 6. It comprises wide section 25, left and right strings 21 and 22, respectively, slit 20, and hole 24. Purse string sutures 26 secure girdle 19 to the aorta. Calcium particles 29 are shown deposited on the interior wall of the aorta.

Figure 7:
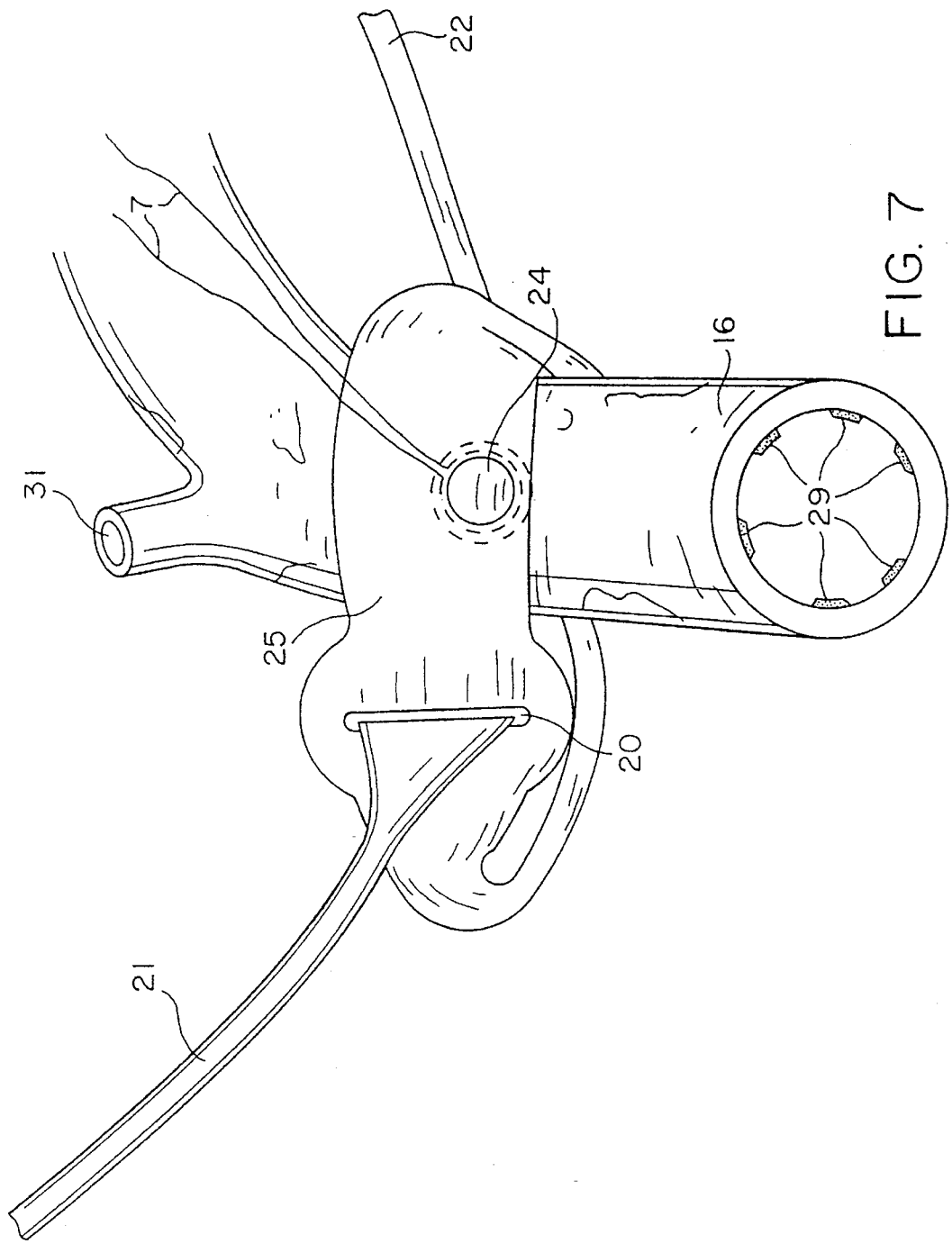
FIG. 7 is a view similar to that of FIG. 6 wherein the girdle has been partly wrapped around the aorta.
Figure 8:
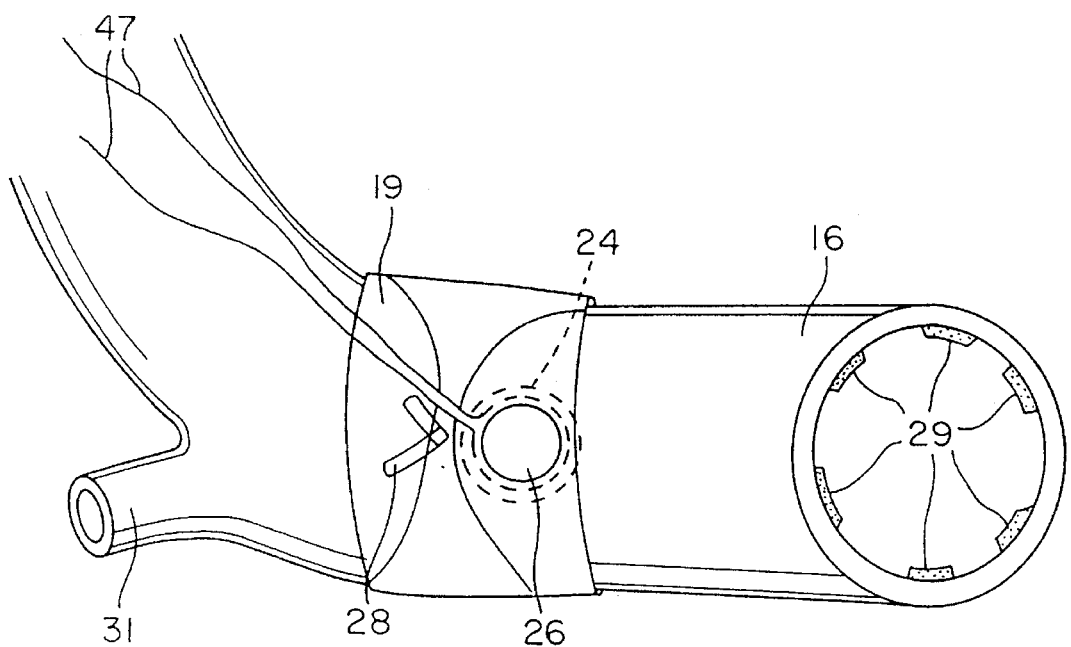
FIG. 8 is a view similar to that FIG. 6 wherein the girdle has been wrapped entirely around the aorta and tied in place.

In practice, girdle 19 is wrapped around the aorta in the direction of arrows 27. Left string 21 is drawn through slot 20 as shown in FIG. 7, and right strap 22 is passed underneath the aorta. The final stage is shown in FIG. 8 wherein girdle 19 is completely wrapped around the aorta, sutured thereto and tied at 28. Excess strings 21 and 22 are, of course, cut off.

In a preferred form of the girdle, it is double walled and has a silicone patch between the layers. This permits the insertion of a blood pressure sensing tube which may remain in the aorta even after the operation is complete. It enables accurate monitoring of the blood pressure during postoperative treatment. When the sensor is to be removed, it is simply pulled out; the opening which it leaves in the wall of the aorta is sealed by the silicone, thereby virtually eliminating any internal bleeding resulting therefrom.

Figure 9:
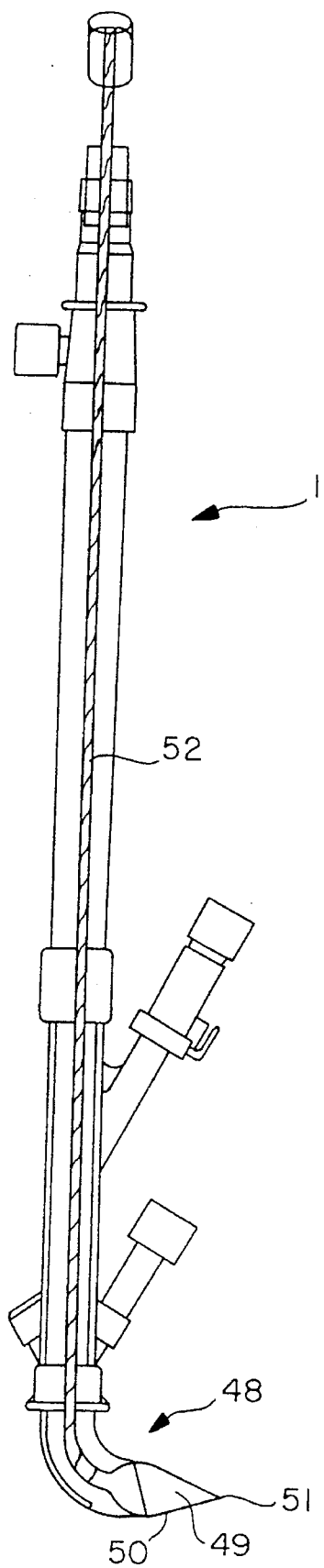
FIG. 9 is a schematic view, partly in section, of the cannula of the present invention with a trocar within.

Referring now to FIG. 9, there is provided hollow trocar 48, having head 49 and point 51. Holes 50 are in head 49 to allow the passage of blood therethrough and guide wire 52 is located within trocar 48. Air and blood pass through holes 50 into the rear portion of trocar 48 and leak out between wire 52 and plug 35. After all the air has been discharged, cannula 1 is clamped when trocar 48 is almost withdrawn. Plug 35 is removed and cannula 1 is connected to the perfusion line of a cardiopulmonary bypass. Thereafter, the clamp is released so that the perfused blood can circulate within the patient.

While only a limited number of specific embodiments of the present invention have been expressly disclosed, it is, nonetheless, to be broadly construed and not to be limited except by the character of the claims appended hereto.

I claim:

1. A perfusion cannula for insertion into an artery, a main channel fluidly connected to an intra-aortic portion of said cannula, said main channel in fluid connection with an aortic perfusion line of a cardiopulmonary bypass, said portion having a proximal end adjacent said main channel and a distal end remote from said main channel, a first side port adapted for fluid connection to a balloon pump at a remote end and in fluid connection with said portion at a near end, a blood pressure port fluidly connected to a blood pressure monitoring tube, said tube being within said portion and extending to a pressure point upstream of said distal end, said tube being adapted for connection to a blood pressure monitoring device and a girdle surrounding a part of said artery, said cannula extending through said girdle into said artery.

2. The cannula of claim 1 comprising a locator ring on said cannula surrounding said cannula to indicate proper location of said cannula in said artery.

3. The cannula of claim 1 wherein said girdle is a substantially rectangular strip of material.

4. The cannula of claim 1 wherein said girdle has a hole therein for entry of said cannula into said artery.

5. The cannula of claim 4 wherein said girdle comprises a first layer, a second layer, and a silicone patch therebetween, thereby to seal an opening in said artery caused by withdrawal of a monitoring element therefrom.

6. The cannula of claim 5 wherein said element monitors blood pressure.

7. The cannula of claim 1 wherein said pressure point is adjacent said distal end.

8. The cannula of claim 1 comprising an inflatable occlusive balloon surrounding at least a part of said portion, said first port fluidly connected to said occlusive balloon and adapted for connection to an extra-aortic pump and to a control device for said intra-aortic pump or said extra-aortic pump.

9. The cannula of claim 8 wherein said girdle is a substantially rectangular strip of material.

10. The cannula of claim 8 wherein said girdle has a hole therein for entry of said cannula into said artery.

11. The cannula of claim 10 wherein said girdle comprises a first layer, a second layer, and a silicone patch therebetween, thereby to seal an opening in said artery caused by withdrawal of a monitoring element therefrom.

12. The cannula of claim 1 wherein said artery comprises an ascending aorta, a descending aorta, and an aortic arch therebetween, a non-occlusive balloon surrounding said portion at or adjacent said distal end and in said descending aorta, said occlusive balloon being adjacent said proximal end, said portion carrying perfused blood extending through said non-occlusive balloon to an exit at or adjacent its distal terminus, whereby said blood passes through said exit in a direction substantially parallel to walls of said descending aorta.

13. The cannula of claim 1 comprising a plug in said first side port at an end remote from said near end, said plug having a one-way valve therein adapted to prevent flow away from said near end and permit flow toward said near end.

14. The cannula of claim 13 wherein said valve permits entry of an intra-aortic balloon catheter therethrough.

15. The cannula of claim 8 wherein said fluid is an aqueous saline.

16. The cannula of claim 12 wherein said non-occlusive balloon is soft and minimizes dislodgment of calcium deposits from said aortic arch.

17. A trocar for use with the cannula of claim 1 comprising a hollow flexible tube within said cannula, a flexible guide wire in said tube, a head at an inner end of said trocar, said head ending in a point adapted for insertion into said artery, said head having at least one hole adapted to allow blood and/or air to flow therethrough toward an outer end of said cannula between said wire and said plug, whereby air is removed from said artery.

18. The method of claim 13 wherein said cannula contains a trocar axially movable therein and having a pointed head,
   insertion of said head into said artery through said incision, thereby dilating said incision, partially withdrawing said trocar after insertion of said cannula, and fully withdrawing said trocar after clamping said cannula.

19. The method of claim 13 comprising placing a girdle around said artery before said introduction, said girdle having a pair of relatively narrow elongated fastening ties, one at either end of said girdle, wrapping said girdle around said artery and tying said ties to secure said girdle.

20. The method of claim 19 wherein said girdle is provided with a hole for admission of said cannula, stitching said girdle to said aorta adjacent said hole before inserting said cannula.

21. A method of introduction of a cannula into an aortic artery, said cannula comprising a main channel fluidly connected to an intra-aortic portion of said cannula, said main channel in fluid connection with an aortic perfusion line of a cardiopulmonary bypass, said portion having a proximal end adjacent said main channel and a distal end remote from said main channel, a first side port adapted for fluid connection to a balloon pump at a remote end and in fluid connection with said portion at a near end, a blood pressure port fluidly connected to a blood pressure monitoring tube, said tube being within said portion and extending to a pressure point upstream of said distal end, said tube being adapted for connection to a blood pressure monitoring device, said method comprising making an incision in a wall of said artery, inserting said cannula through said incision into said artery, clamping said cannula to prevent blood loss, and inflating said cannula.

* * * * *